(12) United States Patent
Modarresi

(10) Patent No.: US 10,478,798 B2
(45) Date of Patent: Nov. 19, 2019

(54) METHANOL SYNTHESIS PROCESS LAYOUT FOR LARGE PRODUCTION CAPACITY

(71) Applicant: Haldor Topsøe A/S, Kgs. Lyngby (DK)

(72) Inventor: Hassan Modarresi, Lyngby (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 16/083,549

(22) PCT Filed: Mar. 23, 2017

(86) PCT No.: PCT/EP2017/056973
§ 371 (c)(1),
(2) Date: Sep. 10, 2018

(87) PCT Pub. No.: WO2017/167642
PCT Pub. Date: Oct. 5, 2017

(65) Prior Publication Data
US 2019/0126231 A1      May 2, 2019

(30) Foreign Application Priority Data

Mar. 30, 2016    (DK) ................... 2016 00192

(51) Int. Cl.
| | | |
|---|---|---|
| B01J 8/06 | (2006.01) | |
| B01J 19/24 | (2006.01) | |
| C07C 29/152 | (2006.01) | |
| B01J 8/02 | (2006.01) | |

(52) U.S. Cl.
CPC ........... *B01J 19/242* (2013.01); *B01J 8/0257* (2013.01); *B01J 8/0278* (2013.01); *B01J 8/06* (2013.01); *C07C 29/152* (2013.01); *B01J 2208/0053* (2013.01); *B01J 2208/00176* (2013.01); *B01J 2208/00274* (2013.01); *B01J 2219/00006* (2013.01); *B01J 2219/00018* (2013.01); *B01J 2219/00051* (2013.01)

(58) Field of Classification Search
CPC .................................. B01J 19/242; B01J 8/06
USPC ......................................................... 422/608
See application file for complete search history.

(56) References Cited

U.S. PATENT DOCUMENTS

| | | |
|---|---|---|
| 4,372,920 A | 2/1983 | Zardi |
| 4,423,022 A | 12/1983 | Albano et al. |

(Continued)

FOREIGN PATENT DOCUMENTS

| | | |
|---|---|---|
| AU | 2013257470 A1 | 5/2014 |
| CN | 105399604 A | 3/2016 |

(Continued)

*Primary Examiner* — Huy Tram Nguyen
(74) *Attorney, Agent, or Firm* — Blank Rome LLP

(57) ABSTRACT

A process layout for large scale methanol synthesis comprises one or more boiling water reactors and one or more radial flow reactors in series, the boiling water reactor(s) being fed with approximately fresh make-up syngas. The methanol synthesis loop comprises a make-up gas compressor K1, a recycle gas compressor K2, two or more boiling water converters for methanol synthesis (A1, A2, . . . ), a radial flow converter (B) for methanol synthesis, a steam drum (V1), a high pressure separator (V2), a low pressure separator (V3), feed effluent heat exchangers (E1 and E2), a wash column (C), an air cooler (E3) and a water cooler (E4).

5 Claims, 1 Drawing Sheet

(56) References Cited

U.S. PATENT DOCUMENTS

| | | | | |
|---|---|---|---|---|
| 4,976,928 A | * | 12/1990 | Foster | B01J 8/0005 |
| | | | | 422/148 |
| 5,512,599 A | * | 4/1996 | Hiramatsu | C01B 3/382 |
| | | | | 518/703 |
| 5,520,891 A | | 5/1996 | Lee | |
| 5,631,302 A | * | 5/1997 | Konig | B01J 8/0488 |
| | | | | 252/373 |
| 7,588,740 B1 | | 9/2009 | Guarino et al. | |
| 8,513,314 B2 | * | 8/2013 | Thorhauge | B01J 8/009 |
| | | | | 518/700 |

FOREIGN PATENT DOCUMENTS

| | | |
|---|---|---|
| EP | 1 262 228 A1 | 12/2002 |
| WO | WO 2009/106231 A1 | 9/2009 |

\* cited by examiner

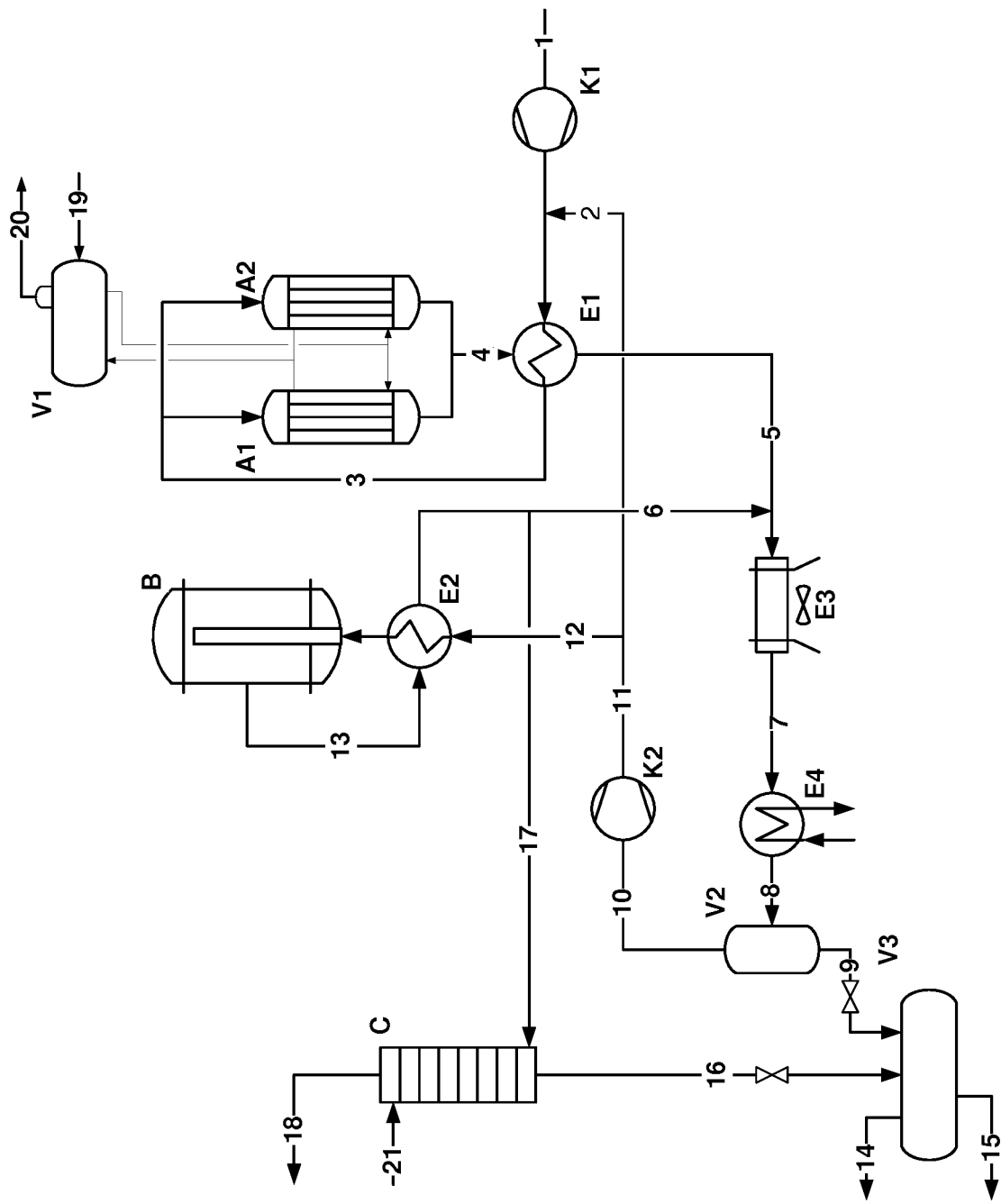

METHANOL SYNTHESIS PROCESS LAYOUT FOR LARGE PRODUCTION CAPACITY

The present invention relates to a novel process layout for a methanol synthesis loop, which is suitable for large scale methanol production plants, i.e. a production capacity above 1000 MTPD and preferably above 5000 MTPD of methanol.

The capacity of methanol plants is constantly increasing to reduce investments, taking advantage of the economy-of-scale. Thus, the capacity of a world scale methanol plant has increased from 2500 MTPD a couple of decades ago to around 5000 MTPD today. Even larger plants are considered to further improve economy and to provide the feedstock for the methanol-to-olefin (MTO) process.

A methanol plant can be divided into three main sections: In the first section of the plant, a feed gas such as natural gas is converted into synthesis gas. The synthesis gas reacts to produce methanol in the second section, and then methanol is purified to the desired purity in the third section in the tail-end of the plant.

The capital cost of large scale methanol plants is substantial. The synthesis gas production, including compression and oxygen production when required, may account for 60% or more of the investment. In many plants today, either tubular steam reforming or two-step reforming is used for the production of synthesis gas. However, stand-alone autothermal reforming at a low steam-to-carbon (S/C) ratio is the preferred technology for large scale plants by maximizing the single-line capacity and minimizing the investment; see for example applicant's WO 2015/128456 A1 describing a stand-alone autothermal reformer for use in producing synthesis gas, e.g. for methanol production.

Stand-alone autothermal reforming (ATR) is a technology used for the production of synthesis gas in which the conversion of a hydrocarbon feedstock or the conversion of a partly converted gas from a pre-reforming step into synthesis gas is completed in a single reactor by the combination of partial combustion and adiabatic steam reforming. Combustion of a hydrocarbon feed is carried out with sub-stoichiometric amounts of air, enriched air or oxygen by flame reactions in a burner combustion zone. Steam reforming of the partially combusted hydrocarbon feedstock is subsequently conducted in a fixed bed steam reforming catalyst.

Stand-alone ATR combines sub-stoichiometric combustion and catalytic steam reforming in one compact refractory-lined reactor to produce synthesis gas for large scale methanol production. The stand-alone ATR operates at a low S/C ratio, thus reducing the flow through the plant and minimizing the investment. The stand-alone ATR produces a synthesis gas well suited for production of both fuel grade and high purity methanol; see for example applicant's WO 2013/013895 A1.

The design of the methanol synthesis section is essential. The optimal design and the choice of operating parameters depend on the desired product specification. In many plants, boiling water reactors (BWRs) are used. However, the use or incorporation of adiabatic reactors may be advantageous.

Methanol is synthesized from synthesis gas (syngas), which consists of $H_2$, CO and $CO_2$. The conversion from syngas is performed over a catalyst, which is most often a copper-zinc oxide-alumina catalyst. The methanol synthesis by conversion from syngas can be formulated as a hydrogenation of carbon dioxide, accompanied by the shift reaction, and it can be summarized by the following reaction sequence comprising the reactions:

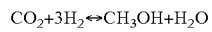

$$CO_2 + 3H_2 \leftrightarrow CH_3OH + H_2O$$

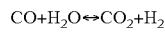

$$CO + H_2O \leftrightarrow CO_2 + H_2$$

The conversion is, as already mentioned, performed over a copper-zinc oxide-alumina catalyst. Examples of this catalyst include applicant's catalysts MK-121 and MK-151 FENCE™.

Because of the widespread use of methanol, especially as the feedstock for the manufacture of other chemicals, the worldwide methanol production is huge, and methods and plants for large scale production are therefore in high demand. However, large methanol plants are subject to the constraints imposed by size limitations on reactors and process equipment. To allow scale-up, the ability to process major amounts of synthesis gas in comparatively small pieces of process equipment has become increasingly important. Thus, in Studies in Surface Science and Catalysis 147, 7-12 (2004) it was demonstrated that this objective could be achieved by combining methanol synthesis technology consisting of combined methanol synthesis and condensation (CMSC) and syngas technology comprising an ATR operating at a very low S/C ratio.

Countries which are rich in coal and natural gas resources for syngas preparation have devoted much effort to the development of large scale methanol production plants. These are largely based on a low pressure methanol synthesis reactor with uniform temperature described in CN 1847208 A.

In US 2009/0018220 A1 to Johnson Matthey PLC, a process for methanol synthesis from a synthesis gas, which is deficient in hydrogen, is disclosed. US 2011/0065966 A1 to Lurgi GmbH discloses a process and a plant for producing methanol, where the synthesis gas is passed through a first, preferably water-cooled reactor, in which a part of the carbon oxides is converted to methanol. Then the obtained mixture is fed to a second, preferably gas-cooled reactor, in which a further part of the carbon oxides is converted to methanol.

To achieve a maximum methanol yield even with an aged catalyst, a partial stream of the synthesis gas is bypassed the first reactor and introduced directly into the second reactor.

In U.S. Pat. No. 8,629,191 B2, Lurgi GmbH describes a process and a plant for producing methanol. The synthesis gas is passed through a first, water-cooled reactor in which a part of the carbon oxides is catalytically converted to methanol. The resulting mixture containing synthesis gas and methanol vapor is fed to a second, gas-cooled reactor in which a further part of the carbon oxides is converted to methanol.

Subsequently, methanol is separated from the synthesis gas, which is then recycled to the first reactor. The cooling gas flows through the second reactor co-current to the mixture withdrawn from the first reactor.

US 2010/0160694 A1 to Johnson Matthey PLC discloses a process for methanol production comprising (a) passing a synthesis gas mixture consisting of a loop gas and a make-up gas through a first synthesis reactor containing a methanol synthesis catalyst, said reactor being cooled by boiling water under pressure, to form a mixed gas containing methanol, (b) cooling the mixed gas containing methanol, (c) passing said cooled mixed gas through a second synthesis reactor containing a methanol synthesis catalyst in which further methanol is synthesized to form a product gas stream, (d) cooling said product gas to condense methanol and (e) recovering the methanol and returning unreacted gas as the loop gas to the first synthesis reactor, wherein the mixed gas containing methanol from the first synthesis reactor is cooled in heat exchange with either said loop gas or said make-up gas.

A large-scale methanol synthesis process is disclosed in CN 103232321 A. In the process, raw material gas first enters a buffering tank, such that partial liquid is removed. Then the gas enters a synthetic gas compressor to be pressurized and subjected to desulfurization in a fine-desulfurization protection bed. The synthetic gas discharged from the fine-desulfurization protection bed is divided into two flows: A first synthetic gas flow is mixed with a second circulation gas flow, heat exchange is carried out, and the mixture enters a first synthesis reactor. After reaction, the high-temperature gas enters a first gas/gas heat exchanger to be subjected to heat exchange with fed gas. Then the gas enters a crude methanol heater for heating crude methanol, the circulation gas is cooled and crude methanol is separated, such that a first circulation gas flow is formed.

The first circulation gas flow is mixed with the second synthetic gas flow, the mixture is pressurized and heated, and enters a second synthesis reactor. High-temperature gas discharged from the second synthesis reactor is cooled and delivered into a second separator; crude methanol is separated, and the second circulation gas flow is formed. The scale of the device can reportedly be enlarged to between 2.000.000 and 2.400.000 ton of methanol product per year, and a one-path conversion rate can reach 7-13 percent.

CN 105399604 A describes a process for the production of methanol, where a stream of synthesis gas is passed through a compressor and two heat exchangers before being split into two streams, each of which enters a water-cooled methanol reactor. These two methanol reactors are arranged in parallel.

Applicant's US 2015/0175509 A1 discloses a process and a reaction system for the preparation of methanol comprising two reaction units, wherein the first unit is operated on a mixture of fresh synthesis gas and unconverted synthesis gas, while the second unit is operated solely with unconverted synthesis gas. The process employs unconverted synthesis gas collected from both the first and the second reaction unit. Thus the recycle gas to both the first and the second unit can be pressurized and circulated by a common circulator, which makes the pressure loss in the recycle stream considerably lower than in other systems comprising two reaction units, because the two reaction units operate at the same pressure.

Basically the present invention concerns a novel process layout for the methanol synthesis loop, offering a number of advantages over the prior art. More specifically, the invention concerns a process layout for methanol synthesis, comprising one or more boiling water reactors and one or more radial flow reactors in series, wherein the boiling water reactor(s) is/are fed with approximately fresh make-up syngas.

This novel process layout for a methanol synthesis loop according to the present invention comprises a make-up gas (MUG) compressor K1, a recycle gas compressor K2, two or more boiling water converters (BWCs) for methanol synthesis (A1, A2, ... ), a radial flow converter (B) for methanol synthesis, a steam drum (V1), a high pressure separator (V2), a low pressure separator (V3), feed effluent heat exchangers (E1 and E2), a wash column (C), an air cooler (E3) and a water cooler (E4).

Preferably, the purge gas is split from the effluent product gas as wet gas (including methanol) and washed with water to recover methanol at approximately the synthesis loop pressure. The radial flow reactor temperature is preferably controlled by adjusting the purge gas and hence the level of inert gas in the reactor inlet.

In a preferred embodiment, the radial flow reactor has a structure, which requires no cooling device. Furthermore, it is preferred that only one train of cooling equipment is used.

BRIEF DESCRIPTION OF THE DRAWINGS

The sole FIGURE shows the synthesis loop layout of the present invention.

DETAILED DESCRIPTION OF THE PREFERRED EMBODIMENTS

In the following, the process layout according to the invention will be described with reference to the appended FIGURE. The synthesis loop layout in the FIGURE. consists of make-up gas (MUG) (1), which is pressurized in K1, mixed with a fraction of recycle gas (2) if it is needed (for example during the start-of-run period when the catalysts in the BWRs are extremely active) and pre-heated in E1. The pre-heated flow (3) is introduced into the two (or more) BWCs A1, A2 . . . , from which a product gas (4) is withdrawn and subjected to feed-effluent (F/E) heat exchange in E1. The partly cooled stream (5) from the heat exchanger is mixed with the effluent (6) from the radial flow converter B and further cooled in the air cooler E3. The outlet gas (7) from E3 is water cooled in E4, and the resulting two-phase stream (8) is split into two streams, a liquid stream (9) and a gas stream (10), of which the latter is compressed in K2 to a stream (11).

The pressurized stream (11) is divided into two streams (12 and 2). Stream 2 is a smaller fraction of stream 11 and might be used if it is needed to control the catalyst peak temperature, and consequently the formation of synthesis by-products in the BWRs. Stream 12 is heat exchanged (pre-heated) in the feed-effluent (F/E) heat exchanger E2. The pre-heated gas is introduced into the radial flow converter B, resulting in the effluent product gas 13 which is cooled partly in E2 and added (as stream 6) to the inlet gas to E3. A part of the E2 outlet is drawn as purge gas 17. The purge gas is washed with water 21 in the wash column C to remove mainly methanol from the stream. The methanol-free gas 18 is purged and can be used as fuel.

The washed product 16 is introduced into the low pressure separator V3 along with the crude methanol stream 9 from the high pressure separator V2. As the separator V3 is operating at a low pressure, gases dissolved in crude methanol are released as stream 14. The crude methanol product is sent to a distillation unit for further purification.

The radial flow converter B is an outward radial flow converter with a methanol synthesis catalyst located between the converter shell and the center tube, which is used for gas distribution over the catalyst bed. In this radial flow converter, no cooling device is used. The catalyst temperature from the synthesis reactions heat is merely controlled by adjusting the purge gas flow, i.e. stream 18. The concentration of inert gases is increased in the converter B inlet by reducing the purge gas flow. Due to insignificant pressure drop in converter B, it is possible to run the synthesis loop with a relatively high recycle flow.

Radial flow converters (RFCs) and boiling water converters (BWCs) are well-known pieces of equipment in the chemical industry. The disclosed synthesis loop configuration uses these well-known unit operations in an innovative way, thereby offering a more effective process for methanol synthesis from syngas.

By using the novel process layout for a methanol synthesis loop according to the present invention, a number of advantages over what was previously known are obtained. The main advantages are that:

only two BWCs, instead of three or even four BWCs, are needed for a typical 5000 MTPD methanol synthesis loop;

a potentially low CAPEX (capital expenditure, which is the cost of developing or providing non-consumable parts for the product or system) is obtained compared to a standard synthesis loop with only BWCs;

a high carbon efficiency is seen in the synthesis loop according to the present invention;

a lower pressure drop is observed across the converters, the layout is simple and practical for industrial implementation and only one train of cooling and condensation is needed for two set of converters.

The invention is illustrated further by the example which follows.

EXAMPLE

A natural gas (NG) based methanol synthesis loop according to the invention with a capacity of 5000 MTPD methanol is used. A front-end stand-alone ATR gives a flow of hydrogen enriched (from the hydrogen recovery unit from purge gas) make-up gas (MUG) of 510.000 Nm$^3$/h with the following composition: 69% $H_2$, 21% CO, 8.5% $CO_2$, 1% $CH_4$ and 0.5% $N_2$.

The total volume of methanol catalyst is 174 m$^3$, more specifically split into 108 m$^3$ in the two BWCs and 66 m$^3$ in the RFC. The two BWCs include 11000 tubes in total, each with an inner diameter of 40.3 mm, an outer diameter of 44.5 mm and a length of 7.7 m. In the RFC, the inner diameter of the center tube is 1.0 m, the shell diameter is 3.6 m and the bed height is 7 m.

A synthesis loop operating pressure of 80 kg/cm$^2$ is kept constant from the start-of-run (SOR) to the end-of-run (EOR). The BWT (boiling water temperature) is varied from 225° C. to 260° C. from SOR to EOR.

The catalyst activity loss is assumed to be 60% for the RFC and 65% for the BWCs over an operation time of 4 years.

At the end-of-run (EOR), i.e. after an operation time of 4 years, the stream composition results (in mole %) shown in the following Table 1 were calculated (the stream numbers (S. no) refer to the FIGURE):

TABLE 1

Stream compositions after 4 years of operation

| S. no | $H_2$ | CO | $CO_2$ | $N_2$ | $CH_4$ | MeOH | $H_2O$ |
|---|---|---|---|---|---|---|---|
| 1 | 69.0 | 21 | 8.5 | 0.5 | 1 | 0 | 0 |
| 3 | 66.9 | 11.3 | 5.8 | 5.5 | 10.2 | 0.25 | 0.02 |
| 4 | 61.4 | 6.9 | 5.6 | 6.3 | 11.6 | 7.2 | 1 |
| 10 | 65.7 | 5.6 | 4.1 | 8.6 | 15.6 | 0.4 | 0.03 |
| 13 | 63.5 | 4.8 | 3.4 | 8.9 | 16.1 | 2.3 | 0.9 |
| 18 | 65.1 | 4.9 | 3.5 | 9.2 | 16.6 | 0 | 0.7 |

The product stream 15 from the low pressure separator V3 consisted of 85.7 weight percent crude methanol (corresponding to 5009 MTPD pure methanol). The stream 15 contained 1120 ppmw ethanol and 9 ppm methyl ethyl ketone.

The flow (f) of the individual streams (S) is indicated in Table 2.

TABLE 2

Flow of individual streams*

| 1 | 2 | 3 | 4 | 6 | 10 | 12 | 13 | 14 | 18 |
|---|---|---|---|---|---|---|---|---|---|
| 510 | 867 | 1377 | 1210 | 3315 | 4335 | 3468 | 3342 | 3 | 26 |

*Upper row: Stream no., lower row: Flow (×1000 Nm$^3$/h)

The power and duty of respectively compressors and heat exchangers used in this production unit are listed as follows:
Compressors
K1: 39.7 MWe K2: 12.5 MWe (both 65% efficiency)
Heat exchangers
E1: 75 MW E2: 256 MW E3: 143 MW E4: 50 MW The synthesis loop carbon efficiency drops slightly from 98.6% at SOR to 97% at EOR (after 4 years of operation). The pressure drop of the catalyst beds in RFC and BWCs increase from 0.1 and 0.9 bar to 0.3 and 1.8 bar, respectively.

The invention claimed is:

1. A process layout for a methanol synthesis loop comprising;
   a first gas compressor for pressurizing a make-up gas,
   two or more boiling water converters for receiving the pressurized make-up gas and outputting a product gas,
   a first heat exchanger for cooling the product gas and pre-heating the make-up gas,
   a high pressure separator for separating the cooled product gas into a liquid stream and a gas stream,
   a second gas compressor for compressing the gas stream,
   a second heat exchanger for pre-heating the compressed gas stream,
   a radial flow reactor for receiving pre-heated compressed gas stream and outputting an effluent product gas, the effluent product gas being partly cooled in the second heat exchanger and added, in part, to the product gas from the boiling water converters, wherein a second part of the effluent product gas is drawn as a purge gas,
   a wash column for washing the purge gas with water to remove methanol, resulting in a methanol-free gas and a washed product, and
   a low pressure separator for receiving the washed product and the cooled liquid stream from the high pressure separator, separating out gases, and outputting a crude methanol product.

2. A process layout for a methanol synthesis loop according to claim 1, wherein the purge gas is split from the effluent product gas as wet gas (including methanol) and washed with water in the wash column to recover methanol at approximately the synthesis loop pressure.

3. A process layout for a methanol synthesis loop according to claim 1, wherein the radial flow reactor temperature is controlled by adjusting the purge gas and hence the level of inert gas in the reactor inlet.

4. A process layout for a methanol synthesis loop according to claim 1, wherein the radial flow reactor has a structure which requires no cooling device.

5. A process layout for a methanol synthesis loop according to claim 1, wherein only one train of cooling equipment is used.

* * * * *